United States Patent
Ray et al.

(10) Patent No.: US 10,466,157 B1
(45) Date of Patent: Nov. 5, 2019

(54) SYSTEM AND METHOD FOR MEASURING CLOUD PARAMETERS

(71) Applicant: Rosemount Aerospace Inc., Burnsville, MN (US)

(72) Inventors: Mark Ray, Burnsville, MN (US); Kaare Josef Anderson, Farmington, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 49 days.

(21) Appl. No.: 15/971,986

(22) Filed: May 4, 2018

(51) Int. Cl.
*G01N 15/14* (2006.01)
*G01W 1/00* (2006.01)

(52) U.S. Cl.
CPC ..... *G01N 15/1434* (2013.01); *G01N 15/1456* (2013.01); *G01W 1/00* (2013.01); *G01W 2203/00* (2013.01)

(58) Field of Classification Search
CPC .................................................. G01N 15/1434
USPC ......................................................... 356/342
See application file for complete search history.

(56) References Cited

U.S. PATENT DOCUMENTS 4,722,599 A * 2/1988 Fruengel ............... G01S 17/107
356/5.06
6,813,020 B2   11/2004 Roques et al.
2004/0027570 A1 * 2/2004 Caldwell ................ B64D 43/00
356/338
2010/0110431 A1 * 5/2010 Ray .......................... B64D 15/20
356/342
2011/0188029 A1 * 8/2011 Schmitt .................... G01S 17/95
356/28
2012/0274938 A1 * 11/2012 Ray ......................... B64D 15/20
356/342
2017/0168161 A1 * 6/2017 Shapira ............... G06F 16/3322
2018/0052237 A1   2/2018 Ray et al.

FOREIGN PATENT DOCUMENTS

CN          106249252 A    12/2016

* cited by examiner

*Primary Examiner* — Tarifur R Chowdhury
*Assistant Examiner* — Omar H Nixon
(74) *Attorney, Agent, or Firm* — Kinney & Lange, P.A.

(57) ABSTRACT

Apparatus and associated methods relate to determining a size and/or density of Super-cooled Large Droplets (SLDs) in a cloud atmosphere by simultaneously projecting both a collimated pulsed beam into a narrow-field projection volume and a divergent pulsed beam into a wide-field projection volume of the cloud atmosphere, and then detecting both the collimated and divergent pulsed beams backscattered from within a detection volume of the cloud atmosphere. Projection and detection are configured such that the detection volume intersects both the narrow-field and the wide-field projection volumes defining narrow-field/detection and wide-field/reception detection volumes, respectively. A distance between the narrow-field/detection intersecting volume and the generating and detecting apparatus is greater than a predetermined distance, thereby avoid detection of light backscattered from within the atmosphere located in a disturbance region of the cloud atmosphere within the predetermined distance from the apparatus.

20 Claims, 7 Drawing Sheets

SYSTEM AND METHOD FOR MEASURING CLOUD PARAMETERS

BACKGROUND

Various cloud conditions can present risks to aircraft when traveling through them. If the temperature of a cloud atmosphere is below the freezing point for water, water droplets can become super-cooled liquid droplets. These super-cooled liquid droplets can then undergo a liquid-to-solid phase change upon impact with an aircraft surface. Ice accretes at different surface regions for different sizes of the super-cooled liquid droplets in the cloud atmosphere. Thus, characterizing the sizes of super-cooled water droplets in a cloud atmosphere can facilitate prediction of surface regions where ice will accrete as well as providing alerts of potentially dangerous conditions to a pilot.

Super-cooled small water droplets tend to form ice only on leading edges of an aircraft's exterior surface. Super-cooled Large water Droplets (SLDs), however, can strike the leading edge of a wing and run back past the icing protection systems, or can traverse airflow vectors and strike surfaces aft of these leading edges. Ice that forms on unprotected surface regions can severely alter the aerodynamics of the aircraft. Such ice accretion may cause aircraft stall or result in unpredictable aircraft control variation that might lead to flight issues. When in a cloud, ice can form on control surfaces and/or lift surfaces.

Not every cloud, however, has a significant SLD population. Different clouds and different atmospheric conditions may be accompanied by various water droplet size distributions, different ice/liquid ratios, etc., some of which may be entirely safe to an aircraft, while others may not be safe. Such water droplet size distributions and ice/liquid ratios may be measured as cloud metrics using various types of instruments.

Some aircraft are equipped with Light Detection and Ranging (LIDAR) systems to measure cloud metrics. Such systems can characterize clouds that have water droplets that have a size distribution having a single mode. Either the mean droplet size or the mode droplet size can be calculated by inversion of a backscatter signal using such systems. These systems can also calculate the density of water droplets for such mono-modal distributions.

Multi-modal distributions of water droplet sizes, however, can be difficult to characterize. Such multi-modal distributions may occur, for example, when cumulus clouds drop drizzle or rain into a lower stratiform cloud deck, creating icing conditions. For droplet size distributions having a dominant mode and a secondary mode (e.g. large concentration of relatively small water droplets plus a small concentration of large water droplets), it can be difficult to detect the anomalous amounts of large water droplets in the secondary mode.

LIDAR systems project pulses of a collimated laser beam into the cloud atmosphere and then sense the signal backscattered by the cloud atmosphere. The collimated laser beam samples a relatively small volume of the cloud, due to the collimated beam having a small field of view (e.g., 4 mrad of divergence is not atypical). Sampling such a small cloud volume can result in the beam encountering few, if any of the SLDs of a secondary distribution.

Depending on the size and density of the SLDs in the secondary distribution, the backscatter signal can appear as scintillation spikes superimposed on an otherwise smooth continuous range-resolved backscatter signal characteristic of the primary distribution. The size and frequency of occurrence of the scintillation spikes depends on the sizes and concentrations of the SLDs and on the volume of space probed by the collimated laser beam.

Unlike the smooth range-resolved backscatter signal from the primary distribution, backscatter signals from small concentrations of large droplet can have randomly occurring scintillation spikes. Averaging of such backscatter signals over multiple laser pulses, while boosting the signal-to-noise ratio of the sparse droplet contribution, can cause the sporadic scintillation spikes from the sparse large droplet concentration to be attenuated, and perhaps even fall below a noise floor. Thus, the SLDs, which can be hazardous to aircraft, may not be sensed.

Mono-modal distributions of SLDs can also be problematic, if the density of SLDs is small. Again, the backscatter signal can be characterized by scintillation spikes randomly located in the temporal stream of backscatter signals. Averaging of such backscatter signals can result in signal amplitude that falls below an instrument's noise floor or is not otherwise invertible. Such a small signal may even fall below an instrument noise floor. Measurement techniques and instruments, which can more accurately characterize water droplet distributions, are needed.

SUMMARY

Apparatus and associated methods relate to a system for measuring cloud parameters. The system includes a pulsed light projector configured to simultaneously project both a collimated pulsed beam along a projection axis into a narrow-field projection volume of a cloud atmosphere and a divergent pulsed beam into a wide-field projection volume of the cloud atmosphere. The system also includes an optical detector aligned so as to detect both the collimated pulsed beam and the divergent pulsed beam simultaneously projected into the cloud atmosphere and backscattered from within a detection volume of the cloud atmosphere, the detection volume aligned with a detection axis different from the projection axis. The detection volume intersects both the narrow-field and the wide-field projection volumes defining narrow-field/detection and wide-field/detection intersecting volumes, respectively. A distance between the narrow-field/detection intersecting volume and the optical detector is greater than a predetermined distance. The optical detector is further configured to generate a signal indicative of the detected pulsed beams backscattered from within both the narrow-field/detection and wide-field/detection intersecting volumes.

Some embodiments relate to a method for measuring cloud parameters. The method includes simultaneously projecting, via a pulsed light projector, both a collimated pulsed beam along a projection axis into a narrow-field projection volume of a cloud atmosphere and a divergent pulsed beam into a wide-field projection volume of the cloud atmosphere. The method includes detecting, via an optical detector, both the collimated pulsed beam and the divergent pulsed beam simultaneously projected into the cloud atmosphere and backscattered from within a detection volume of the cloud atmosphere. The detection volume is aligned with a detection axis different from the projection axis. The detection volume intersects both the narrow-field and the wide-field projection volumes defining narrow-field/detection and wide-field/reception detection volumes, respectively. A distance between the narrow-field/detection intersecting volume and the system is greater than a predetermined distance. The method includes generating, via the optical detector, a signal indicative of the detected pulsed beam backscattered from within both the narrow-field/detection and wide-field/reception detection volumes. The method also includes determining, via a processor and based at least in part on the signal indicative of the detected pulsed beam, a metric of Super-cooled Large Droplets (SLDs).

DETAILED DESCRIPTION

Apparatus and associated methods relate to determining a size and/or density of Super-cooled Large Droplets (SLDs) in a cloud atmosphere by comparing detected light signals reflected from small and large sampling volumes of a cloud atmosphere. Sampling the small volume of the cloud atmosphere can complement sampling of the large-volume. A large volume can be probed by projecting a divergent light beam into the cloud atmosphere. The divergent light beam will then be backscattered by the water particles of the cloud atmosphere. The large volume will contain a relatively large number of such backscattering water particles, which will produce a temporally smoothly-varying backscattered light signal. A small volume can be probed by projecting a collimated light beam into the cloud atmosphere. Again, the projected light beam will be backscattered by water particles within the cloud atmosphere. Because only a relatively small volume of the atmosphere is probed by the collimated beam, the backscattering events will be much fewer in number as compared with the number of such events when probing a large volume. The resulting light signal backscattered by the relatively few backscattering events will produce a light signal characterized by scintillation spikes. Each scintillation spike can correspond to a backscattering event from a single water particle. The backscattered beams from both the large and small sampling volumes can be used in conjunction with one another to provide various metrics of the cloud atmosphere.

Figure 1:
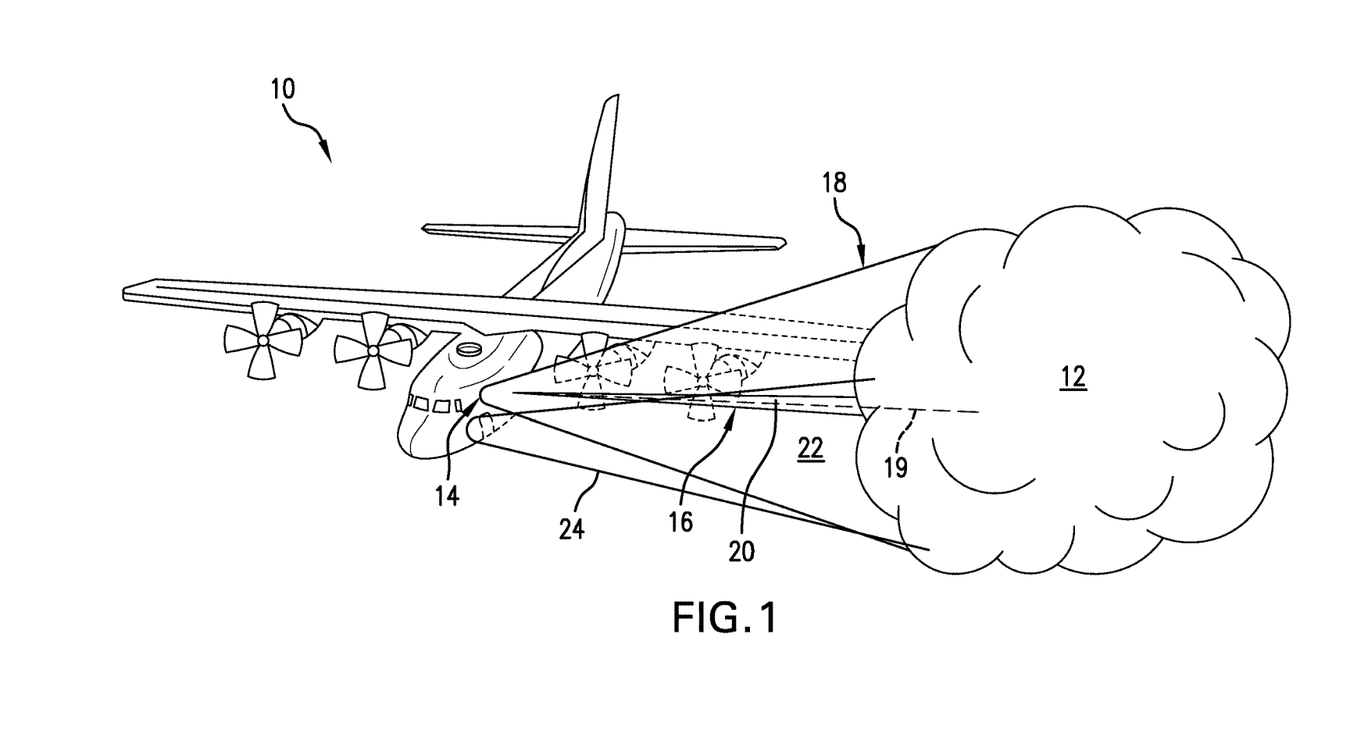
FIG. 1 is a schematic view of an aircraft using an exemplary cloud conditions measurement system that projects both a collimated pulsed beam and a divergent pulsed beam into a cloud atmosphere.

FIG. 1 is a schematic view of an aircraft using an exemplary cloud conditions measurement system that projects both a collimated pulsed beam and a divergent pulsed beam into a cloud atmosphere. In FIG. 1, aircraft 10 is traveling through cloud atmosphere 12. Aircraft 10 is equipped with cloud conditions measurement system 14 that is probing cloud atmosphere 12 by projecting both collimated pulsed beam 16 along projection axis 19 and divergent pulsed beam 18 about projection axis 19. The collimated and divergent pulsed beams 16 and 18 are projected from a pulsed beam projector aligned with projection axis 19.

Collimated pulsed beam 16 has a relatively small divergence and is projected into first narrow-field projection volume 20 of cloud atmosphere 12. In some embodiments, the divergence of collimated portion 16 can be characterized by an angle of divergence of 4 mrad, for example. Cloud atmosphere 12, which, if sampled over a depth of ten meters by such a collimated pulsed beam 16, for example, would result in a first probe volume 20 being equal to about $5 \times 10^{-3}$ m$^3$.

Divergent pulsed beam 18 has a relatively large divergence and is projected into wide-field projection volume 22. In some embodiments, the divergence of divergent pulsed beam 18 can be a result of projection from an optical system having a concave diverging lens, for example. Cloud atmosphere 12, which, if sampled over a depth of ten meters by such a divergent pulsed beam 18 again, would result in second probe volume 22 being equal to about 0.5 m$^3$. Thus, wide-field projection volume 22 is more than a hundred times larger than narrow-field projection volume 20.

Each of the collimated and divergent pulsed beams 16 and 18 can be backscattered by water droplets and ice crystals of cloud atmosphere 12. Portions of the pulsed beams 16 and 18 backscattered by cloud atmosphere 12 can be detected by one or more optical detectors. Such optical detectors can be configured to detect light backscattered from within detection volume 24. The depicted detection volume results from using an optical detector that is not coaxial with projection axis 19 but is laterally separated from projection axis 19. Because of this lateral separation between the pulsed light projector and the optical detector, detection volume 24 intersects narrow-field and wide-field projection volumes 20 and 22 beginning at a predetermined distance from the pulsed light projector and optical detector. Thus, any light detected by the optical detector is backscattered by water particles that are located at least the predetermined distance from aircraft 10. The optical detectors can then generate an electrical signal corresponding to the detected optical energy so backscattered by cloud atmosphere 12. These generated electrical signals are indicative of various metrics of cloud atmosphere 12.

If only the divergent pulsed beam 18 is projected into and backscattered by cloud atmosphere 12, a relatively large volume—wide-field projection volume 22—of cloud atmosphere 12 from which water droplets backscatter the pulses of optical energy is sampled. This large volume is likely to have water particles distributed fairly uniformly throughout the sampled volume. Even should the particle density be relatively modest, such a large sample volume would likely have many particles well distributed throughout the range distances from the optical source. When large volumes of cloud atmosphere 12 are sampled using such a divergent-beam LIDAR system, backscattering results from a great many water droplets, which are encountered at many range locations from the location where the pulsed beams of light are emitted. The corresponding backscatter signal that is generated when sampling such a large volume can be a smooth continuous range-resolved backscatter signal, with the range corresponding to photonic round-trip flight time (e.g., time for light to travel from an optical source to a backscattering water droplet within the sampling volume, plus the return time to an optical detector).

If, however, only the collimated pulsed light beam 16 were projected into and backscattered by cloud atmosphere 12, a relatively small volume—narrow-field projection volume—of cloud atmosphere 12 is sampled. When small volumes of cloud atmosphere 12 are sampled using such a collimated-beam LIDAR system, backscattering results from the relatively rare illumination of a water droplet. Each backscattering event is generated at a specific range location from the location where the pulses of light are emitted. The corresponding backscatter signal that will be generated when sampling such a small volume will be a series of scintillation spikes generated at each round-trip flight time of each of the light pulses.

In such small-sample-volume scenarios, the generated signal indicative of various cloud metrics can be marked with scintillation spikes, each corresponding to a round trip flight time of the light pulse to and from a particular water droplet. Even when probing small sample volumes, many, if not most, clouds have so many small droplets distributed throughout the sampling volume that the generated backscatter signal is relatively smooth and continuous. Scintillation spikes usually result from Super-cooled Large Droplets (SLDs). SLDs are often found in clouds having a bimodal distribution, with the primary mode including small droplets. In such bimodal cloud scenarios, the signal detected when sampling small volumes of bimodally-distributed water droplets can have scintillation spikes superimposed upon a smooth continuous range-resolved backscatter signal. The scintillation spike portion of the backscatter signal principally results from SLD backscattering, while the smooth continuous portion of the backscatter signal results from backscattering from small but densely-distributed droplets.

Thus, obtaining signals facilitating the isolation of both the smooth continuous and the scintillation-spike portions of the backscatter signal can facilitate determination of metrics of both the primary-mode droplets and the secondary-mode droplets.

Figure 2A:
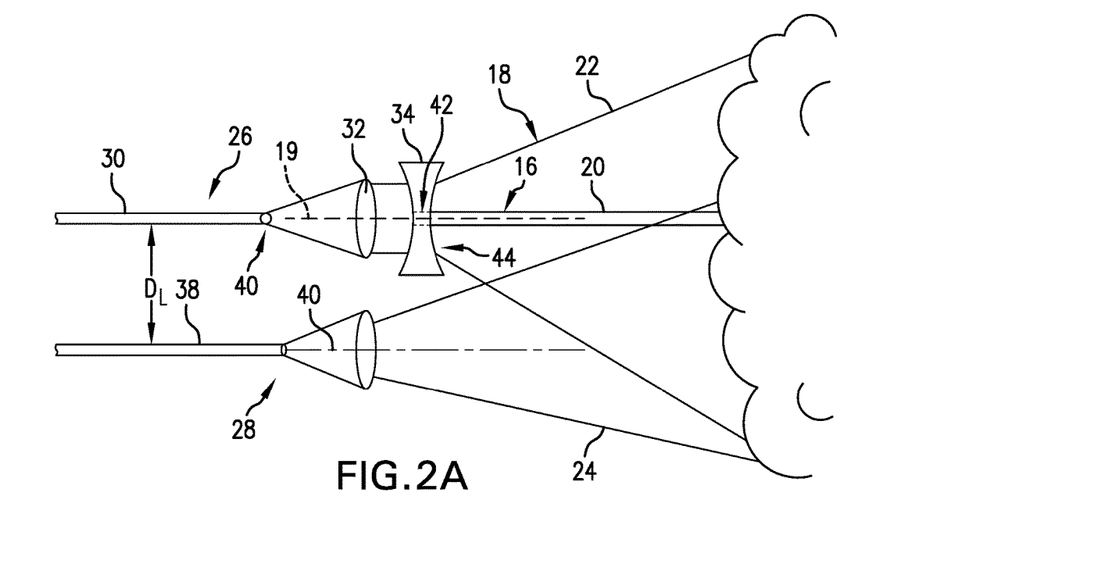
FIG. 2A is a schematic diagram of an embodiment of a cloud conditions measurement system that simultaneously generates both collimated and divergent pulsed beams (e.g., light beams).

FIG. 2A is a schematic diagram of an embodiment of a cloud conditions measurement system that simultaneously generates both collimated and divergent pulsed beams (e.g., light beams). In FIG. 2A, cloud conditions measurement system 14 is depicted probing cloud atmosphere 12. Cloud conditions measurement system 14 includes pulsed beam projector 26 and optical detector 28. Pulsed beam projector 26 includes first optical fiber 30, collimating lens 32 (e.g., convex lens), diverging lens 34 (e.g., concave lens). Optical detector 28 includes detection lens 36 and second optical fiber 38. In the depicted embodiment, first optical fiber 30 receives a pulsed beam from a pulsed beam source, such as, for example, a laser diode. First optical fiber 30 transmits the received pulsed beam to first end 40, from which pulsed beam is divergently projected.

The pulsed beam that is divergently projected from first end 40 of first optical fiber 30 is collimated by collimating lens 32. The collimated beam then encounters diverging lens 34, which has central region 42 and annular outer region 44. Central region 42 is configured to pass a central portion of the collimated beam in such a manner that the central portion remains collimated and is projected along projection axis 19. Collimated pulsed beam 16 is projected in this manner into narrow-field projection volume 20. Annular outer region 44 is configured to refract an annular outer portion of the collimated beam in such a manner so as to diverge the refracted beam in an annular fashion about projection axis 19. Divergent pulsed beam 18 is projected in this manner into wide-field projection volume 22.

Optical detector 28 is configured to detect the projected collimated and divergent pulsed beams 16 and 18 backscattered from within detection volume 24. Optical detector 28 is laterally separated from pulsed beam projector 26 by lateral separation distance $D_L$. In the depicted embodiment, detection axis 46 is parallel to projection axis 19. Optical detector 28 detects the projected collimated and divergent pulsed beams 16 and 18 backscattered by cloud atmosphere 12. Because of the lateral separation distance $D_L$ between pulsed beam projector 26 and optical detector 28, detection will arise only for light backscattered from within the intersections of projection volumes 20 and 22 and detection volume 24.

Both collimated and divergent pulsed beams 16 and 18 are received and subsequently detected by optical detector 28. Divergent pulsed beam 18 is projected into wide-field projection volume 22, which is comparatively large with respect to narrow-field projection volume 20 into which collimated pulsed beam 16 is projected. The relatively large sampling volume (i.e., the portion of the projection volume that contributes to a detectable signal of the projected optical energy backscattered by the cloud atmosphere) ensures that virtually all of the droplets in the cloud, small or large, are illuminated, and from which the laser pulse is backscattered and subsequently detected. Sampling such a large number of droplets results in a smooth, continuous range-resolved backscatter signal. Even should the cloud have a bimodal distribution of droplet sizes, the contribution of large droplets may still be too small to result in a backscatter signal that can be differentiated from one caused by a monomodal small-droplet cloud.

Conversely, collimated pulsed beam 16 is projected into narrow-field projection volume 20, which is comparatively small, with respect to wide-field projection volume 22 into which divergent pulsed beam 18 is projected. The relatively small sampling volume ensures that a relatively modest number of droplets in the cloud, small or large, are illuminated and their backscatter detected. Sampling such a small number of droplets results in scintillation spikes superimposed on an otherwise smooth, continuous, range-resolved backscatter signal. A cloud that has a bimodal distribution of droplet sizes can thereby be differentiated, via the scintillation spikes, from a monomodal small-droplet cloud.

Figure 2B:
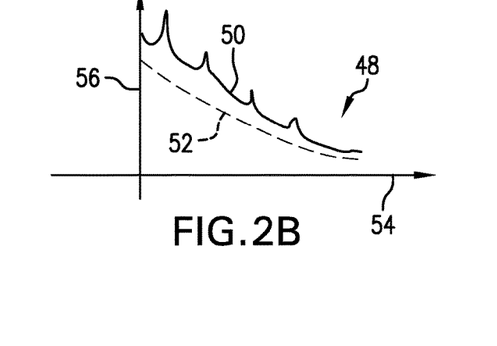
FIG. 2B is a graph of exemplary backscatter signals resulting from both collimated and divergent pulsed beams.

FIG. 2B is a graph of exemplary backscatter signals resulting from both collimated and divergent portions of a light beam. In FIG. 2B, graph 48 includes two range-resolved backscatter signals 50, 52. First range-resolved backscatter signal 50 corresponds to a projected pulsed beam having both collimated and divergent portions. Second range-resolved backscatter signal 52 corresponds to a pulsed beam having only a divergent portion. Graph 48 has horizontal axis 54, which is indicative of range within cloud atmosphere 12 from which the projected optical energy is backscattered. Graph 48 has vertical axis 56, which is indicative of intensity of the detected backscatter signal. Note that backscatter signal 50 includes scintillation spikes corresponding to the collimated portions of the projected pulses of optical energy. Note also that backscatter signal 52 has no scintillation spikes due to the absence of signal contribution corresponding to a collimated sampling volume.

Figure 3:
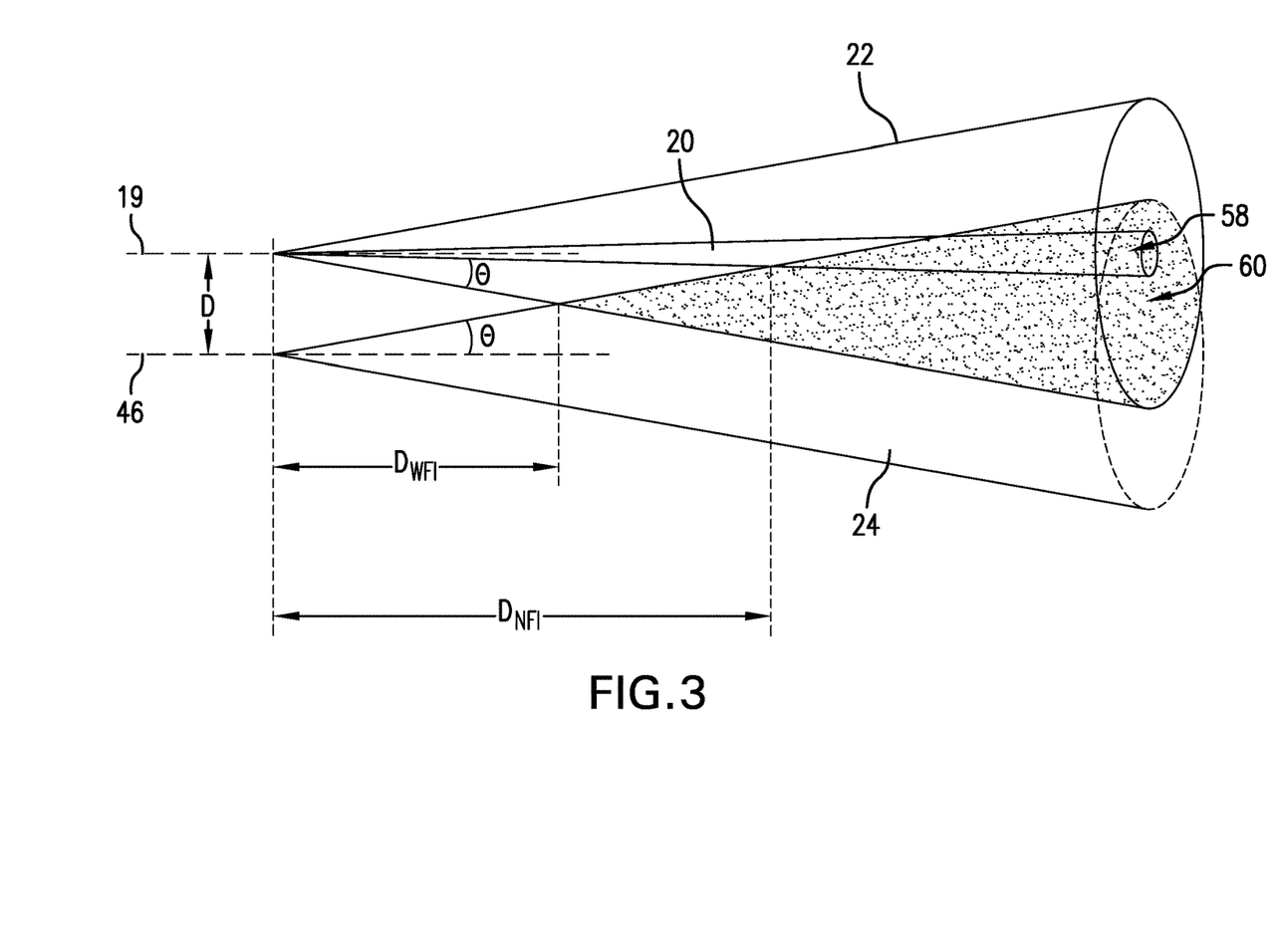
FIG. 3 is a schematic diagram that illustrates the relationship between the projection field of view and the detection field of view for an embodiment of an optical cloud conditions measurement system having a projector laterally separated from a detector.

FIG. 3 is a schematic diagram that illustrates the relationship between the projection field of view and the detection field of view for an embodiment of an optical cloud conditions measurement system having a projector laterally separated from a detector. In FIG. 3, narrow-field projection volume 20 and wide-field projection volume 22 are shown in relation to projection axis 19. Narrow-field projection volume 20 is depicted as a cone characterized by a small angle of divergence. Wide-field projection volume 22 is depicted as an annular conic section formed by a volume defined between an outer cone and an inner cone. The outer cone defining the annular conic section of wide-field projection volume 22 has a characteristic angle θ with respect to projection axis 19. Detection volume 24 is shown in relation to detection axis 46. Detection volume 24 is the volume within a cone having a characteristic angle φ with respect to detection axis 46.

Narrow-field/detection intersection volume 58 is defined by the intersection of narrow-field projection volume 20 and detection volume 24. Collimated pulsed beams projected and backscattered within narrow-field/detection intersection volume 58 can be detected by a cloud conditions measurement system configured with such narrow-field projection and detection volumes 20 and 24. Narrow-field/detection intersection volume 58 is located at distance $D_{NFI}$ from the pulsed beam source and optical detector so configured. Wide-field/detection intersecting volume 60 is defined by the intersection of wide-field projection volume 22 and detection volume 24. Divergent pulsed beams projected and backscattered within wide-field/detection intersection volume 60 can be detected by a cloud conditions measurement system configured with such wide-field projection and detection volumes 22 and 24. Wide-field/detection intersection volume 60 is located at distance $D_{WFI}$ from the pulsed beam source and optical detector so configured. Both wide- and narrow-field intersecting volumes 58 and 60 are remote from the pulsed beam source and optical detector so as to exclude detection of light backscattered within a predetermined distance of an aircraft to which the cloud measurement system is mounted.

Figure 4:
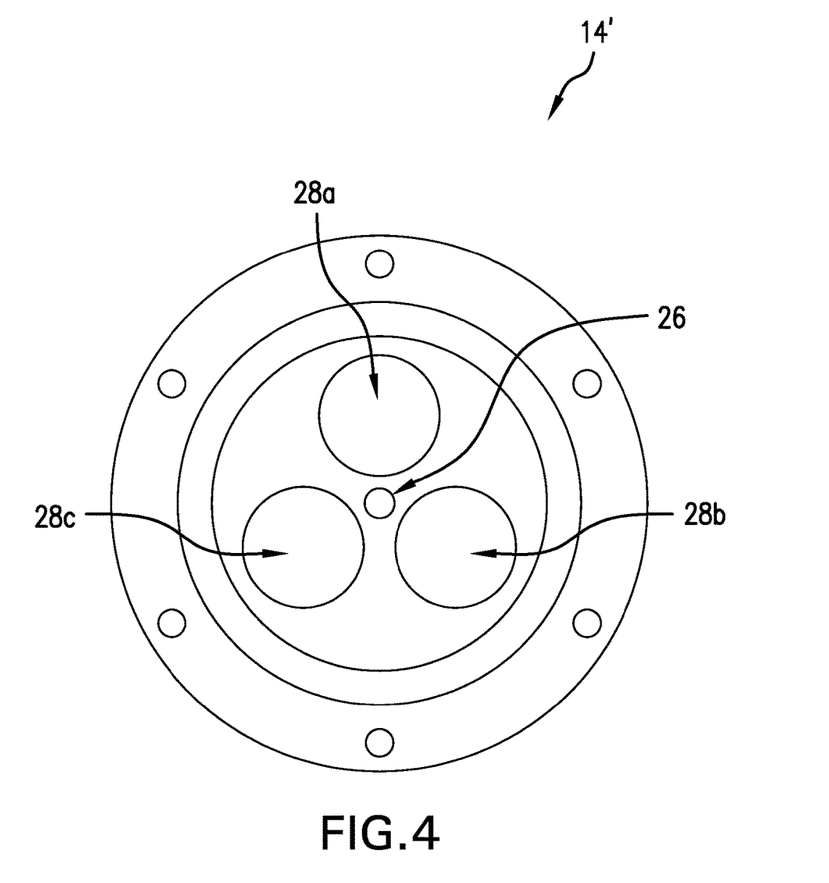
FIG. 4 is an axial view of an embodiment of cloud conditions measurement system that has three detectors axially distributed about a projector.

FIG. 4 is an axial view of an embodiment of cloud conditions measurement system that has three detectors axially distributed about a projector. In FIG. 4, cloud conditions measurement system 14' includes pulsed beam projector 26 and optical detectors 28A, 28B and 18C. Pulsed beam projector 26 is centered within optical detectors 28A, 28B and 28C, which are distributed on a circle centered on pulsed beam projector 26. Pulsed beam projector 26 is configured to project collimated and divergent beams 16 and 18 into narrow- and wide-field projection volumes 20 and 22, respectively. Optical detectors 28A, 28B and 28C are configured to detect light from within detection volumes 24A, 24B and 24C, respectively.

Each of optical detectors 28A, 28B and 28C can be configured to measure a different optical signal. For example, optical detector 28A can be configured to detect light of a first circular polarity and a first wavelength. Optical detector 28B can be configured to detect light of a second circular polarity and the first wavelength. Optical detector 28C can be configured to detect light of a second wavelength, for example.

Figure 5:
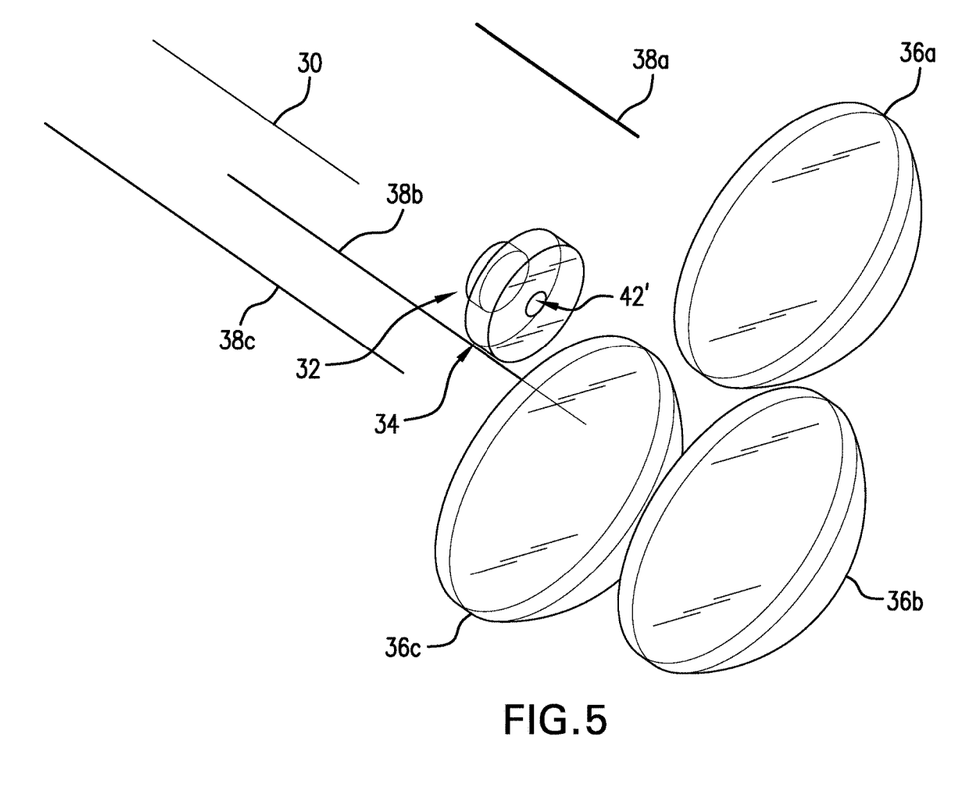
FIG. 5 is a schematic diagram of an embodiment of optical systems for the triple detector embodiment depicted in FIG. 4.

FIG. 5 is a schematic diagram of an embodiment of optical systems for the triple detector embodiment depicted in FIG. 4. In FIG. 4, cloud conditions measurement system 14' includes pulsed beam projector 26 and optical detectors 28A, 28B and 28C. Pulsed beam projector 26 includes transmitter fiber 30, collimating lens 32, diverging lens 34 with central hole 42'. In some embodiments, an optical emitter is located at the remote end of transmitter fiber 30. In other embodiments, an optical emitter is located proximate lenses 32 and 34 so as to generate and project pulsed beams directly onto and through lenses 32 and 34. Optical detector 28A includes detection lens 36A and receiver fiber 38A. Optical detector 28B includes detection lens 36B and receiver fiber 38B. Optical detector 28C includes detection lens 36C and receiver fiber 38C. In some embodiments, optical sensors are located at remote ends of receiver fibers 38A, 38B and 38C so as to detect optical signals focused onto proximate ends and transmitted by receiver fibers 38A, 38B and 38C. In other embodiments, detection lenses 36A, 36B and 36C focus light directly onto optical sensors.

Figure 6:
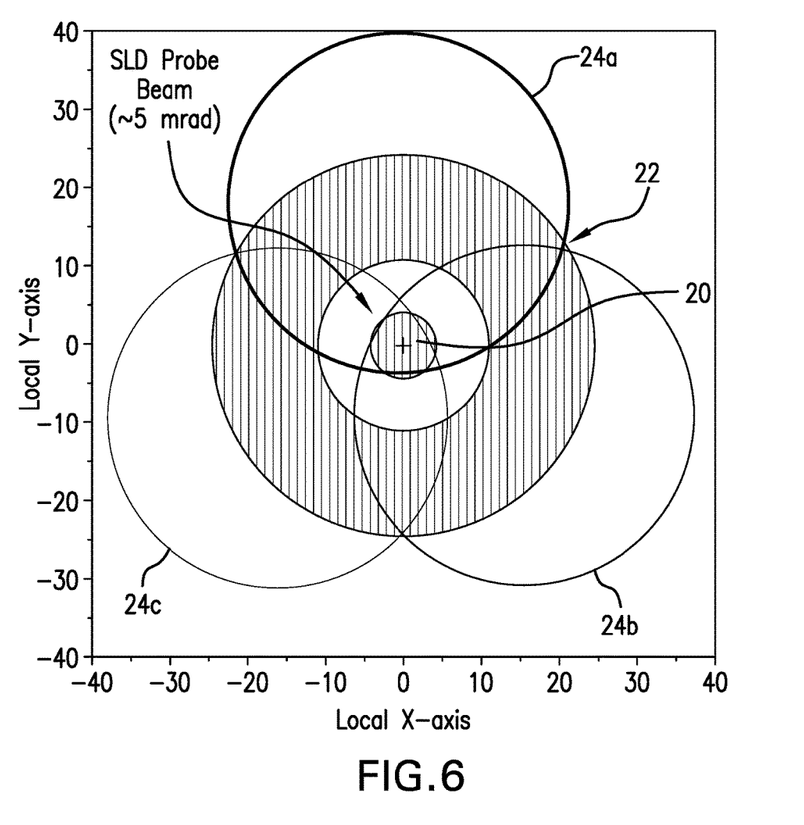
FIG. 6 is a cross-sectional slice of the projection and detection volumes corresponding to the triple detector embodiment depicted in FIGS. 4A-5.

FIG. 6 is a cross-sectional slice of the projection and detection volumes corresponding to the triple detector embodiment depicted in FIGS. 4-5. In FIG. 6, narrow-field projection volume 20 is centrally located about projection axis 19. Wide-field projection volume 22 is annularly located about narrow-field projection volume 20. Detection volumes 24A, 24B and 24C are centered about detection axes 46A, 46B and 46C, respectively. Each of detection volumes 24A, 24B and 24C intersects both narrow- and wide-field projection volumes 20 and 22. Because the detection volumes 24A, 24B and 24C are depicted as intersecting both narrow- and wide-field projection volumes 20 and 22, the FIG. 6 image is a cross-sectional slice at a distance of at least $D_{NFI}$ to narrow-field/detection intersection volume 58 (depicted in FIG. 3).

Figure 7:
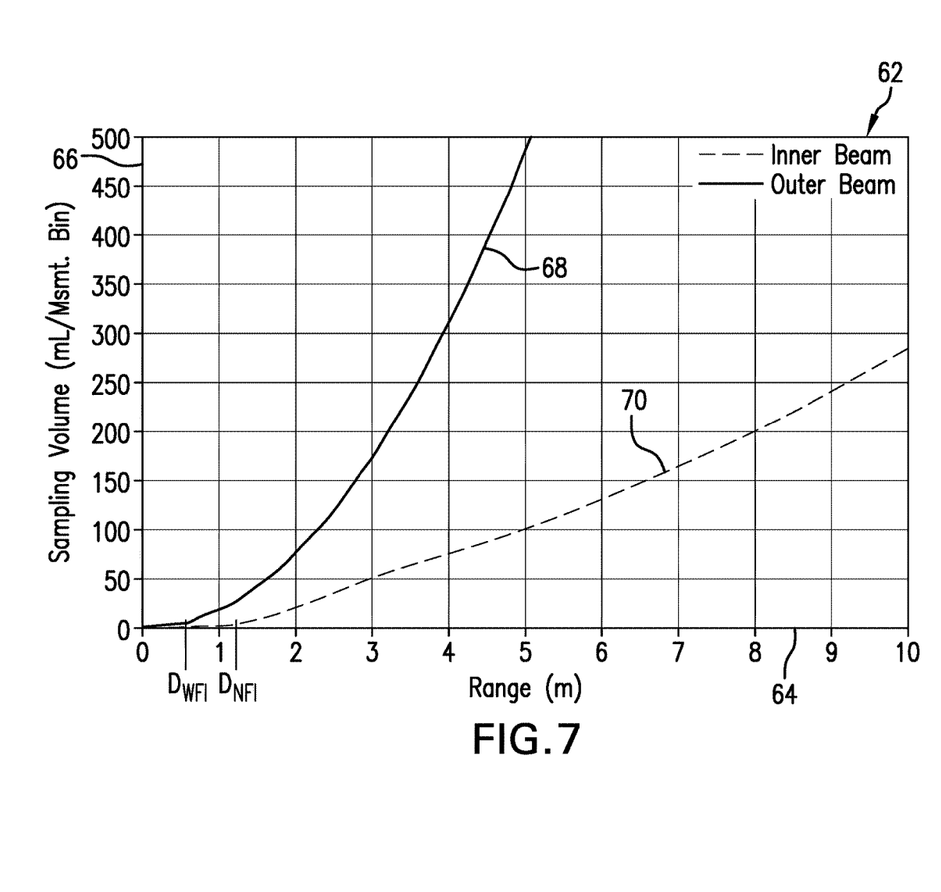
FIG. 7 is a graph of the collimated and divergent marginal volumes as a function of distance from the projector and detectors of the triple detector embodiment depicted in FIGS. 4A-5.

FIG. 7 is a graph of the collimated and divergent marginal projection volumes as a function of distance from the projector of the triple detector embodiment depicted in FIGS. 4A-5. In FIG. 7 graph 62 includes horizontal axis 64, vertical axis 66, wide-field marginal projection volume 60 (depicted in FIG. 3) vs. range relation 68 and narrow-field marginal projection volume 58 (depicted in FIG. 3) vs. range relation 70. Horizontal axis 62 is indicative of range corresponding to the marginal projection volume. Vertical axis 64 is the calculated projection marginal volume. The marginal projection volume is the projection volume corresponding to a delta about the range. Relation 68 depicts a relationship between range and wide-field marginal projection volume 60. Note that the wide-field marginal projection volume 60 is zero below the distance $D_{WFI}$ to the wide-field marginal projection volume 60. Relation 70 depicts a relationship between range and narrow-field marginal projection volume 58. A ratio of the wide-field to narrow-field marginal projection volumes 60 to 58 can be controlled by a size of the center region 42 of diverging lens 34 depicted in FIG. 2A. In some embodiments size of center region 42 can be controllable so as to control the ratio of the wide-field to narrow-field/detection intersecting volumes 60 to 58.

Discussion of Possible Embodiments

The following are non-exclusive descriptions of possible embodiments of the present invention.

Apparatus and associated methods relate to a system for measuring cloud parameters. The system includes a pulsed light projector configured to simultaneously project both a collimated pulsed beam along a projection axis into a narrow-field projection volume of a cloud atmosphere and a divergent pulsed beam into a wide-field projection volume of the cloud atmosphere. The system also includes an optical detector aligned so as to detect both the collimated pulsed beam and the divergent pulsed beam simultaneously projected into the cloud atmosphere and backscattered from within a detection volume of the cloud atmosphere, the detection volume aligned with a detection axis different from the projection axis. The detection volume intersects both the narrow-field and the wide-field projection volumes defining narrow-field/detection and wide-field/detection intersecting volumes, respectively. A distance between the narrow-field/detection intersecting volume and the optical detector is greater than a predetermined distance. The optical detector is further configured to generate a signal indicative of the detected pulsed beams backscattered from within both the narrow-field/detection and wide-field/detection intersecting volumes.

The system of the preceding paragraph can optionally include, additionally and/or alternatively, any one or more of the following features, configurations and/or additional components:

A further embodiment of the foregoing system, wherein the projection axis and the detection axis can be substantially parallel to one another and separated from one another by the product of a distance between the system and the narrow-field/detection intersecting volume and the tangent of an angle defining a conic section commensurate with the detection volume.

A further embodiment of any of the foregoing systems, wherein a plane perpendicular to the projection axis can intercept both a projection lens of the pulsed light projector and a detection lens of the optical detector.

A further embodiment of any of the foregoing systems, wherein the predetermined distance can be one meter.

A further embodiment of any of the foregoing systems, wherein the pulsed light projector can be further configured to project a circularly polarized pulsed beam having a first wavelength and a second pulsed beam having a second wavelength.

A further embodiment of any of the foregoing systems, wherein the optical detector can be further configured to separately detect and generate a signal indicative of right-hand circularly polarized light of the first wavelength, left-hand circularly polarized light of the first wavelength, and light of the second wavelength.

A further embodiment of any of the foregoing systems, wherein the pulsed light projector can include a circular polarizer configured to circularly polarize both the collimated pulsed beam and the divergent pulsed beam.

A further embodiment of any of the foregoing systems, wherein the divergent pulsed beam can be projected in an annular fashion about the collimated pulsed beam so as to project into an annular conic volume of the cloud atmosphere.

A further embodiment of any of the foregoing systems, wherein the pulsed light projector can include a laser configured to generate a pulse of optical energy. The system can include a first optical fiber configured to transmit, from the laser, the generated pulse of optical energy and to project, from a projection end, the transmitted pulse of optical energy. The system can also include a projection lens aligned with the projection end of the first optical fiber. The projection lens can be configured to both collimate a narrow-field portion and to diverge a wide-field portion of the projected pulse of optical energy so as to project the collimated pulsed beam along the projection axis into a narrow-field projection volume of a cloud atmosphere and the divergent pulsed beam into the wide-field projection volume of the cloud atmosphere.

A further embodiment of any of the foregoing systems, wherein the projection lens can include a collimating lens aligned on the projection axis. The collimating lens can be configured to receive and collimate the pulsed beam of optical energy projected by the projection end of the first optical fiber. The system can also include a diverging lens aligned on the projection axis. The diverging lens can have a center region and an annular outer region. The center region can be configured to pass without diverging a center portion of the collimated beam. The annular outer region can be configured to diverge an annular outer portion of the received collimated beam.

A further embodiment of any of the foregoing systems, wherein the center region of the diverging lens can be an aperture.

A further embodiment of any of the foregoing systems can further include a processor configured to determine, based at least in part on the signal indicative of the detected pulsed beam, a metric of Super-cooled Large Droplets (SLDs).

A further embodiment of any of the foregoing systems, wherein the optical detector can include a detection lens aligned along the detection axis. The detection lens can be configured so as to receive both the collimated pulsed beam and the divergent pulsed beam simultaneously projected into the cloud atmosphere and backscattered from within the detection volume of the cloud atmosphere. The system can include a second optical fiber having a reception end aligned with the detection axis so as to receive, via the detection lens, a portion of the projected pulsed beam backscattered by the cloud atmosphere from within the narrow-field/detection and wide-field/detection intersecting volumes, and to transmit, along a length of the second optical fiber, the received portion of the pulsed beam. The system can also include a detector configured to detect the transmitted portion of the pulsed beam received by the second optical fiber, and to generate a signal indicative of the detected portion.

A further embodiment of any of the foregoing systems, wherein the detection lens can be a first detection lens, the detection axis can be a first detection axis, the detection volume can be a first detection volume, the narrow-field/detection intersecting volume can be a first narrow-field/detection intersecting volume, the wide-field/detection intersecting volume can be a first wide-field/detection intersecting volume, and the detector can a first detector. The system can further include a second detection lens aligned along a second detection axis different from both the projection axis and the first detection axis. The second detection lens can be configured to receive both the collimated pulsed beam and the divergent pulsed beam simultaneously projected into the cloud atmosphere and backscattered from within a second detection volume of the cloud atmosphere. The second detection volume can be aligned with the second detection axis. The second detection volume can intersect both the narrow-field and the wide-field projection volumes defining second narrow-field/detection and second wide-field/reception detection volumes, respectively. The system can include a third optical fiber having a reception end aligned with the second detection axis so as to receive, via the second detection lens, a portion of the projected beam backscattered by the cloud atmosphere from within the second narrow-field/detection and second wide-field/detection intersecting volumes, and to transmit the received portion of optical energy. The system can also include a second detector configured to detect the transmitted portion of the pulsed beam received by the third optical fiber, and to generate a signal indicative of the detected portion.

A further embodiment of any of the foregoing systems can further include a third reception lens aligned along a third reception axis different from the projection axis, the first reception axis and the second reception axis. The third reception lens can be configured to receive light from within a third reception volume aligned with the third reception axis. The third reception volume can intersect both the narrow-field and the wide-field volumes defining third narrow-field/reception and third wide-field/reception intersecting volumes, respectively. A distance between the third narrow-field/reception intersecting volume and the third reception lens is greater than the predetermined distance. The system can include a fourth optical fiber having a reception end aligned with the third reception axis so as to receive, via the third reception lens, a portion of the projected pulse of optical energy backscattered by the cloud atmosphere from within the third narrow-field/reception and third wide-field/reception intersecting volumes, and to transmit the received portion of optical energy. The system can also include a third detector configured to detect the transmitted portion of the pulse of optical energy received by the fourth optical fiber, and to generate a signal indicative of the detected portion.

Some embodiments relate to a method for measuring cloud parameters. The method includes simultaneously projecting, via a pulsed light projector, both a collimated pulsed beam along a projection axis into a narrow-field projection volume of a cloud atmosphere and a divergent pulsed beam into a wide-field projection volume of the cloud atmosphere. The method includes detecting, via an optical detector, both the collimated pulsed beam and the divergent pulsed beam simultaneously projected into the cloud atmosphere and backscattered from within a detection volume of the cloud atmosphere. The detection volume is aligned with a detection axis different from the projection axis. The detection volume intersects both the narrow-field and the wide-field projection volumes defining narrow-field/detection and wide-field/reception detection volumes, respectively. A distance between the narrow-field/detection intersecting volume and the system is greater than a predetermined distance. The method includes generating, via the optical detector, a signal indicative of the detected pulsed beam backscattered from within both the narrow-field/detection and wide-field/reception detection volumes. The method also includes determining, via a processor and based at least in part on the signal indicative of the detected pulsed beam, a metric of Super-cooled Large Droplets (SLDs).

The method of the preceding paragraph can optionally include, additionally and/or alternatively, any one or more of the following features, configurations and/or additional components:

A further embodiment of the foregoing method, wherein projecting the divergent beam can include projecting the divergent pulsed beam in an annular fashion about the collimated pulsed beam so as to project into an annular conic volume of the cloud atmosphere.

A further embodiment of any of the foregoing methods can further include circularly polarizing both the simultaneously projected collimated and divergent pulsed beams.

A further embodiment of any of the foregoing methods, wherein simultaneously projecting both a collimated and a divergent pulsed beam can include generating, via a laser, a pulse of optical energy. Simultaneously projecting both a collimated and a divergent pulsed beam can include transmitting, via a first optical fiber, the generated pulse of optical energy from the laser. Simultaneously projecting both a collimated and a divergent pulsed beam can include projecting, from a projection end of the optical fiber, the transmitted pulse of optical energy. Simultaneously projecting both a collimated and a divergent pulsed beam can include collimating, via a transmission lens aligned with the projection end of the first optical fiber, a narrow-field portion of the projected pulse of optical energy along so as to project the collimated narrow-field portion along a projection axis into a narrow-field volume of a cloud atmosphere. Simultaneously projecting both a collimated and a divergent pulsed beam also can include diverging, via the transmission lens, a wide-field portion of the projected pulse of optical energy so as to project the divergent wide-field portion into a wide-field volume of the cloud atmosphere.

A further embodiment of any of the foregoing methods, wherein detecting both a collimated and a divergent pulsed beam can include receiving, via a reception lens aligned along a reception axis different from the projection axis, light from within a reception volume aligned with the reception axis. The reception volume can intersect both the narrow-field and the wide-field volumes defining narrow-field/reception and wide-field/reception intersecting volumes, respectively. A distance between the narrow-field/reception intersecting volume and the reception lens can be greater than a predetermined distance. Detecting both a collimated and a divergent pulsed beam can include receiving, via a second optical fiber having a reception end aligned with the reception axis, a portion of the projected pulse of optical energy backscattered by the cloud atmosphere from within the narrow-field/reception and wide-field/reception intersecting volumes. Detecting both a collimated and a divergent pulsed beam can include transmitting, via the second optical fiber, the received portion of optical energy. Detecting both a collimated and a divergent pulsed beam also can include detecting, via a detector, the transmitted portion of the pulse of optical energy received by the second optical fiber.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for measuring cloud parameters, the system comprising:
   a pulsed light projector configured to simultaneously project both a collimated pulsed beam along a projection axis into a narrow-field projection volume of a cloud atmosphere and a divergent pulsed beam into a wide-field projection volume of the cloud atmosphere; and
   an optical detector aligned so as to detect portions the projected collimated and divergent pulsed beams that are backscattered from within a detection volume of the cloud atmosphere, the detection volume aligned with a detection axis different from the projection axis,
   wherein the detection volume intersects both the narrow-field and the wide-field projection volumes defining narrow-field/detection and wide-field/detection intersecting volumes, respectively,
   wherein a distance between the narrow-field/detection intersecting volume and the optical detector is greater than a predetermined distance, and
   wherein the optical detector is further configured to generate a signal indicative of the detected portions of the collimated and divergent pulsed beams backscattered from within both the narrow-field/detection and wide-field/detection intersecting volumes.

2. The system of claim 1, wherein the projection axis and the detection axis are substantially parallel to one another and separated from one another by the product of a distance between the system and the narrow-field/detection intersecting volume and the tangent of an angle defining a conic section commensurate with the detection volume.

3. The system of claim 1, wherein a plane perpendicular to the projection axis intercepts both a projection lens of the pulsed light projector and a detection lens of the optical detector.

4. The system of claim 1, wherein the predetermined distance is one meter.

5. The system of claim 1, wherein the pulsed light projector is further configured to project a circularly polarized pulsed beam having a first wavelength and a second pulsed beam having a second wavelength.

6. The system of claim 5, wherein the optical detector is further configured to separately detect and generate a signal indicative of right-hand circularly polarized light of the first wavelength, left-hand circularly polarized light of the first wavelength, and light of the second wavelength.

7. The system of claim 5, wherein the pulsed light projector includes:
a circular polarizer configured to circularly polarize both the collimated pulsed beam and the divergent pulsed beam.

8. The system of claim 1, wherein the divergent pulsed beam is projected in an annular fashion about the collimated pulsed beam so as to project into an annular conic volume of the cloud atmosphere.

9. The system of claim 1, wherein the pulsed light projector includes:
a laser configured to generate a pulse of optical energy;
a first optical fiber configured to transmit, from the laser, the generated pulse of optical energy and to project, from a projection end, the transmitted pulse of optical energy; and
a projection lens aligned with the projection end of the first optical fiber, the projection lens configured to both collimate a narrow-field portion and to diverge a wide-field portion of the projected pulse of optical energy so as to project the collimated pulsed beam along the projection axis into a narrow-field projection volume of a cloud atmosphere and the divergent pulsed beam into the wide-field projection volume of the cloud atmosphere.

10. The system of claim 9, wherein the projection lens includes:
a collimating lens aligned on the projection axis, the collimating lens configured to receive and collimate the pulsed beam of optical energy projected by the projection end of the first optical fiber; and
a diverging lens aligned on the projection axis, the diverging lens having a center region and an annular outer region, the center region configured to pass without diverging a center portion of the collimated beam, the annular outer region configured to diverge an annular outer portion of the received collimated beam.

11. The system of claim 10, wherein the center region of the diverging lens comprises an aperture.

12. The system of claim 1, further comprising:
a processor configured to determine, based at least in part on the signal indicative of the detected pulsed beam, a metric of Super-cooled Large Droplets (SLDs).

13. The system of claim 1, wherein the optical detector includes:
a detection lens aligned along the detection axis, the detection lens configured so as to receive portions of both the projected collimated and divergent pulsed beams that are backscattered from within the detection volume of the cloud atmosphere;
a second optical fiber having a reception end aligned with the detection axis so as to receive, via the detection lens, the portions of the projected collimated and divergent pulsed beams backscattered by the cloud atmosphere from within the narrow-field/detection and wide-field/detection intersecting volumes, and to transmit, along a length of the second optical fiber, the received portions; and
a detector configured to detect the portions of the pulsed beams received and transmitted by the second optical fiber, and to generate a signal indicative of the detected portions.

14. The system of claim 13, wherein the detection lens is a first detection lens, the detection axis is a first detection axis, the detection volume is a first detection volume, the narrow-field/detection intersecting volume is a first narrow-field/detection intersecting volume, the wide-field/detection intersecting volume is a first wide-field/detection intersecting volume, and the detector is a first detector, the system further comprising:
a second detection lens aligned along a second detection axis different from both the projection axis and the first detection axis, the second detection lens configured to receive portions of both the projected collimated and divergent pulsed beams that are backscattered from within a second detection volume of the cloud atmosphere, the second detection volume aligned with the second detection axis wherein the second detection volume intersects both the narrow-field and the wide-field projection volumes defining second narrow-field/detection and second wide-field/reception detection volumes, respectively;
a third optical fiber having a reception end aligned with the second detection axis so as to receive, via the second detection lens, the portions of the projected collimated and divergent pulsed beams backscattered by the cloud atmosphere from within the second narrow-field/detection and second wide-field/detection intersecting volumes, and to transmit the received portions; and
a second detector configured to detect the portions of the pulsed beam received and transmitted by the third optical fiber, and to generate a signal indicative of the detected portions.

15. The system of claim 14, further comprising:
a third detection lens aligned along a third detection axis different from the projection axis, the first detection axis, and the second detection axis, the third detection lens configured to receive portions of both the projected collimated and divergent pulsed beams that are backscattered from within a third detection volume of the cloud atmosphere, the third detection volume aligned with the third detection axis wherein the third detection volume intersects both the narrow-field and the wide-field projection volumes defining third narrow-field/detection and third wide-field/reception detection volumes, respectively;
a fourth optical fiber having a reception end aligned with the third detection axis so as to receive, via the third detection lens, the portions of the projected collimated and divergent pulsed beams backscattered by the cloud atmosphere from within the third narrow-field/detection and third wide-field/detection intersecting volumes, and to transmit the received portions; and a second detector configured to detect the portions of the pulsed beam received and transmitted by the fourth optical fiber, and to generate a signal indicative of the detected portions.

16. A method for measuring cloud parameters, the method comprising:

simultaneously projecting, via a pulsed light projector, both a collimated pulsed beam along a projection axis into a narrow-field projection volume of a cloud atmosphere and a divergent pulsed beam into a wide-field projection volume of the cloud atmosphere;

detecting, via an optical detector, portions of both the projected collimated and divergent pulsed beams that are backscattered from within a detection volume of the cloud atmosphere, wherein the detection volume is aligned with a detection axis different from the projection axis, wherein the detection volume intersects both the narrow-field and the wide-field projection volumes defining narrow-field/detection and wide-field/reception detection volumes, respectively, wherein a distance between the narrow-field/detection intersecting volume and the pulsed light projector and/or from the optical detector is greater than a predetermined distance, generating, via the optical detector, a signal indicative of the detected portions of the collimated and divergent pulsed beams that are backscattered from within both the narrow-field/detection and wide-field/reception detection volumes; and determining, via a processor and based at least in part on the signal indicative of the detected portions, a metric of Super-cooled Large Droplets (SLDs).

17. The method of claim 16, wherein projecting the divergent beam comprises:

projecting the divergent pulsed beam in an annular fashion about the collimated pulsed beam so as to project into an annular conic volume of the cloud atmosphere.

18. The method of claim 16, further comprising:

circularly polarizing both the simultaneously projected collimated and divergent pulsed beams.

19. The method of claim 16, wherein simultaneously projecting both a collimated and a divergent pulsed beam comprises:

generating, via a laser, a pulse of optical energy;

transmitting, via a first optical fiber, the generated pulse of optical energy from the laser;

projecting, from a projection end of the optical fiber, the transmitted pulse of optical energy;

collimating, via a transmission lens aligned with the projection end of the first optical fiber, a narrow-field portion of the projected pulse of optical energy along so as to project the collimated narrow-field portion along a projection axis into a narrow-field volume of a cloud atmosphere; and diverging, via the transmission lens, a wide-field portion of the projected pulse of optical energy so as to project the divergent wide-field portion into a wide-field volume of the cloud atmosphere.

20. The method of claim 16, wherein detecting both a collimated and a divergent pulsed beam comprises:

receiving, via a reception lens aligned along a reception axis different from the projection axis, light from within a reception volume aligned with the reception axis, wherein the reception volume intersects both the narrow-field and the wide-field volumes defining narrow-field/reception and wide-field/reception intersecting volumes, respectively, wherein a distance between the narrow-field/reception intersecting volume and the reception lens is greater than a predetermined distance;

receiving, via a second optical fiber having a reception end aligned with the reception axis, the portions of both the projected collimated and divergent pulsed beams backscattered by the cloud atmosphere from within the narrow-field/reception and wide-field/reception intersecting volumes;

transmitting, via the second optical fiber, the received portions; and detecting, via a detector, the portions of the pulsed beams received and transmitted by the second optical fiber.

* * * * *